[54] COAGULANT PLASMA-PROTEIN SOLUTION

[75] Inventors: Ronald Kotitschke; Wolfgang Stephan, both of Dreieich, Fed. Rep. of Germany

[73] Assignee: Biotest-Serum-Institut GmbH, Frankfurt, Fed. Rep. of Germany

[21] Appl. No.: 561,390

[22] Filed: Dec. 14, 1983

[30] Foreign Application Priority Data

Dec. 21, 1982 [DE] Fed. Rep. of Germany ....... 3247150

[51] Int. Cl.³ .............................................. A61K 35/16
[52] U.S. Cl. .................................................... 424/101
[58] Field of Search ......................................... 424/101

[56] References Cited

U.S. PATENT DOCUMENTS

| | | | |
|---|---|---|---|
| 3,686,395 | 8/1972 | Stephan | 424/101 |
| 3,998,946 | 12/1976 | Condie et al. | 424/101 |
| 4,081,431 | 3/1978 | Stephan et al. | 424/101 |
| 4,272,523 | 6/1981 | Kotitschke et al. | 424/101 |

OTHER PUBLICATIONS

Haemostasis and Thrombosis, Edingburgh, London, Melbourne and New York, Churchill Livingstone, 1981, 472–490.
Fresh Frozen Plasma: Effects and Side Effects, *Bibliotheca haemat.* 46, 189–206, (1980).
Haemostatic Disorders in Massive Transfusion, *Bibliotheca haemat.* 46, 179–188, (1980).
The Surface-Mediated Initiation of Blood Coagulation and Related Phenomena, in Ogston & Bennett, Haemostasis, 1977, 25–55.
Von H. G. Lasch et al., Verbrauchskoagulopathien (Pathogenese und Therapie), *Folia haematologica,* Neue Folge, Bd. 6, pp. 325–330, (1961).

*Primary Examiner*—Sam Rosen
*Attorney, Agent, or Firm*—Sprung, Horn, Kramer & Woods

[57] ABSTRACT

A coagulant plasma-protein solution obtained by adsorbing stabilized human plasma at least once with 20–40 mg of colloidal silicic acid per gram of plasma protein and separating the adsorbent from the adsorbate, a method of manufacturing the solution, and a pharmaceutical preparation containing the solution and intended for the intravenous treatment of complex disorders of the hemostatic system. The solution is low in fibrinogen and factors XI and XII but otherwise close in composition to the starting material.

11 Claims, No Drawings

COAGULANT PLASMA-PROTEIN SOLUTION

BACKGROUND OF THE INVENTION

The present invention relates to a coagulant plasma-protein solution obtained by adsorbing stabilized human plasma at least once with 20–40 mg of colloidal silicic acid per gram of plasma protein and separating the adsorbent from the adsorbate, to a method of manufacturing the solution, and to a pharmaceutical preparation containing the solution and intended for the intravenous treatment of complex disorders of the hemostatic system.

Treating patients suffering from hemostatic malfunctions with blood and blood components has been described in numerous publications [Bloom, A. L. & Thomas, D. P., *Hemostasis and Thrombosis*, Edinburgh, London, Melbourne, and New York, Churchill Livingstone, 1981, 472–90 and Lechner, K., "Rationelle Substitutionstherapie bei Gerinnungstörungen," *Infusionstherapie* 4, 5 (1980), 190–94, for example]. Intravascular malfunction is so manifold in the most various diseases that no uniform theoretical opinion has existed up to now as to the optimal methods of treatment. This is especially due to the practical impossibility of appropriate clinical studies because of the the multiplicity of the different syndromes. In practice, clinical experience has proven blood-component treatment to be successful. The commonest agents of this type are, apart from fresh blood, fresh plasma or fresh-frozen plasma, freeze-dried fresh plasma, platelet concentrate, cryoprecipitate, and the more or less highly purified clotting-factor concentrates like fibrinogen, antihemophilic globulin A (AHG or factor VIII), and the concentrates that contain clotting factor IX, sometimes in combination with factors II, VII, and X (PPSB concentrates).

The problematics of deciding as to the utilization of particular blood components or even particular inhibitors, heparin for instance, is evident in the clinical picture of consumption coagulopathy. Consumption coagulopathy (disseminated or generalized intravascular coagulation) is an acquired blood-clotting disorder characterized by increased consumption of plasma clotting factors and thrombocytes deriving from generalized intravascular coagulation [Lasch, H. G. et al, "Verbrauchskoagulopathien (Pathogenese und Therapie)," *Folia haemat.* (N.F.) 6, 325–30 (1961)]. Causative conditions that can be connected with consumption coagulopathy include bacterial shock, burns, carcinoma, leukemia, amniotic embolism, fat embolism, acidosis, hypoxemia, bacteriemia, virus diseases, organ transplants, and anaphylactic shock.

E. Lechler et al. point out ["Therapie bei Verbrauchskoagulopathie," *Deutsche Medizinische Wochenschrift* 100, 1, 24–25 (1975) that consumption coagulopathy leads to hemorrhagic diathesis and, by way of fibrin precipitation, to microcirculatory disorder accompanied by organic necrosis. Therapy should disrupt the intravascular coagulational process, specifically by treatment of the causative condition or pathogenic mechanism provoking the intravascular coagulation on the one hand and, on the other, by utilizing coagulation-inhibiting agents. This paper recommends heparin therapy for the treatment of consumption coagulopathy. G. Wolff ["Fresh frozen plasma: effects and side effects," *Bibliotheca haemat.* 46, 189–206 (1980)], on the other hand, is of the opinion that fresh frozen plasma is an extremely effective means for treating post-traumatic consumption coagulopathy, whereas treatment with heparin is by no means without danger and its basis is in no way recognized as decisive on a worldwide level. He states that heparin only replaces one kind of coagulation disorder with another and iatrogenic type.

H. Harke and S. Rahmen ["Haemostatic disorders in massive transfusion," *Bibliotheca haemat.* 46, 179–88 (1980)] demonstrated by means of various citations that patients' conditions are frequently not improved by the application of specific blood components but can sometimes even be worsened. They say that diffuse hemorrhagic tendencies based mainly on disruptions of the plasma and/or thrombocyte coagulation systems are among the postoperative complications most to be feared subsequent to massive transfusions. Characteristic changes in the plasma and thrombocyte system subsequent to massive transfusions should also indicate the significant part played by hemorrhagic shock in the occurrence of coagulation disorders. The authors also say that the risk of microembolism accompanied by more or less severe damage to organic perfusion seems to be unavoidable after massive transfusion, so that more attention should be paid from the aspect of organic insufficiency to the high lethality that follows massive transfusions of stored blood due to microembolism and the formation of microaggregates. One component that can lead to considerable deterioration in the clinical situation is fibrinogen in the plasmas, whether out-dated or fresh frozen and even when manufactured in accordance with the latest technical advances, administered to patients [cf. Koerner, K. et al., "Das tiefgefrorene Frischplasma in der Blutkomponententherapie: Herstellung—Qualitätskontrolle—Indikation," *Infusionstherapie* 8, 253–58 (May, 1981)]. The cited studies show that it is fibrin precipitation itself that leads to disruption of the microcirculation accompanied by organic necrosis.

German Pat. Nos. 1 617 319 and 1 617 335 describe methods of manufacturing lipoprotein-free, stable, and sterile sera. Blood serum or plasma is absorbed with 250–500 mg of colloidal silicic acid per gram of total protein at temperatures up to 50° C., the silicic acid is separated, and the serum subjected to ultraviolet radiation and sterilized by filtration. The radiation is carried out under normal conditions—in the air.

European Pat. No. 14 333 describes a method of manufacturing several therapeutically useful plasma-protein preparations. Stabilized blood plasma is adsorbed on 50–400 mg of colloidal silicic acid per gram of plasma protein to harvest the fibrinogen and the fibrinogen-free plasma-protein solution obtained as an intermediate product is then further processed into, in addition to other preparations, a solution of serum proteins that will be stable under storage. The plasma-protein solution obtained as an intermediate product also contains some clotting factor. A citrated plasma treated with propiolactone and ultraviolet radiation (in the air) could be employed as a starting material.

SUMMARY OF THE INVENTION

The object of the present invention is the manufacture of a plasma-protein solution with a considerably decreased fibrinogen content that will nevertheless contain the important labile clotting factors V and VIII and inhibitors, like antithrombin III, unchanged and that is appropriate for the treatment of complex disorders of the hemostatic system.

This object is attained in accordance with the invention with coagulant plasma-protein solution obtained by at least one adsorption of stabilized human plasma with 20–40 mg of colloidal silicic acid per gram of plasma protein followed by separation of the adsorbent from the adsorbate.

It has, surprisingly, been discovered that decreasing the amount of colloidal silicic acid to 20–40 mg per gram of plasma protein when human plasma is adsorbed onto colloidal silicic acid not only sufficiently decreases the fibrinogen content by at least 50% but also can maintain an adequate level of factors V and VIII, and adsorption can be carried out more than once, specifically twice, to further decrease the fibrinogen content.

Table I shows the concentration of clotting factors in the product as a function of the amount of colloidal silicic acid employed in adsorption and compares the adsorption carried out in step 1 of the method described in European Pat. No. 14 333 with that in accordance with the present invention.

TABLE 1

Concentration of clotting factors in the product as a function of the amount of colloidal silicic acid employed in adsorption.

| | Concentration of clotting factors in percent of normal. | | |
|---|---|---|---|
| | Starting material | Following adsorption on | |
| | (citrated plasma) | 250 mg/g[a] | 2 × 40 mg/g[b] of silicic acid |
| Factor II | 100 | 95 | 100 |
| Factor V | 100 | 10 | 95 |
| Factor VII | 100 | 92 | 100 |
| Factor VIII | 100 | 20 | 90 |
| Factor IX | 100 | 98 | 100 |
| Factor X | 100 | 95 | 100 |
| Factor XI | 100 | 0 | 10 |
| Factor XII | 100 | 0 | 10 |
| Antithrombin III | 100 | 98 | 100 |
| Fibrinogen (mg/100 ml) | 300 | 0 | 30 |

[a] Single adsorption on 250 mg of silicic acid per gram of protein as in EP 14 333.
[b] Two successive adsorptions on 40 mg of silicic acid per gram of protein each.

As Table 1 indicates, the plasma-protein solution in accordance with the invention and obtained by adsorption on less colloidal silicic acid than specified in European Pat. No. 14 333 and German Pat. Nos. 1 617 319 and 1 617 335 contains normal concentrations of all the clotting factors with the exception of the problematic fibrinogen, which is to be removed from the plasma in accordance with the invention, and of the surface-active factors XI and XII.

An especially surprising result that is associated with the manufacture of low-fibrinogen fresh plasma by utilizing colloidal silicic acid to adsorb the fibrinogen is the finding, summarized in Table II, that the adsorbancy of factor VIII onto colloidal silicic acid varies with the concentration of silicic acid.

TABLE II

Concentration of fibrinogen and factor VIII in the plasma as a function of the concentration of colloidal silicic acid during adsorption.

| mg of silicic acid per g of protein | Factor VIII activity | % of standard antigen | mg of fibrinogen per 100 ml |
|---|---|---|---|
| 0 Starting plasma | 100 | 100 | 300 |
| 500[a] 1st adsorption | 0 | 0 | 0 |
| 40 2nd adsorption | 95 | 95 | 150 |
| 40 | 90 | 90 | 30 |

[a] As in German Patent 1 617 319

The data in Table II again indicate that the controlled utilization of specific amounts of colloidal silicic acid in plasma adsorption in accordance with the invention results in an almost fibrinogen-free plasma-protein solution that still contains the essential clotting factors.

The starting material in the method in accordance with the invention is a stabilized human plasma obtained by stabilizing human blood by adding citrate stabilizers, heparin, or other known stabilizers or by the extraction of calcium ions with ion exchangers by the method described in German Pat. No. 2 459 291 and centrifuging the erythrocytes off.

It is practical for the colloidal silicic acid employed for adsorption to have a specific surface of 50–400 $m^2/g$.

The adsorbent is preferably separated from the adsorbate after adsorption onto colloidal silicic acid by filter sterilization or ultrafiltration.

The plasma-protein solution in accordance with the invention has many advantages over known fresh plasmas. One reason for the need to employ fresh plasmas in the form prevalent up to now is that they cannot be filter-sterilized in large quantities because they contain fibrinogen. The plasma-protein solution in accordance with the invention can be filter-sterilized in large volumes even on an industrial scale because much of the fibrinogen has been removed from the plasma by being adsorbed onto the colloidal silicic acid. One reason that fresh plasma have had to be stored deep-frozen is that freeze-dried plasmas containing fibrinogen are difficult to dissolve. The fibrinogen in the plasmas cannot be brought into solution easily and, frequently, completely.

The plasma-protein solution in accordance with the invention can be freeze-dried and subsequently reconstituted into a clear and particle-free solution.

The volume of water added to dissolve the freeze-dried proteins can be varied and even decreased to obtain the high level of clotting-factor activity that results when a lot of protein is dissolved in only a little water.

The potential for pooling various fresh plasmas and processing them into a plasma-protein solution in accordance with the invention provides another advantage in comparison with the use of individual donor plasmas in that the blood-group compatibility of the donor and recipient does not need to be established. Combining the plasmas obtained from separate donors into a large pool dilutes the various blood-group antibodies of the ABO system to the extent that the plasma can be used with any blood type.

That factor XII (the Hageman factor) is adsorbed onto the colloidal silicic acid along with the fibrinogen in the method in accordance with the invention is another significant advantage of the plasma-protein solution in accordance with the invention over conventional fresh plasmas because factor XII is one of the proteins that may normally be absent during hemostasis

[cf. Ratnoff, O.D., "The surface-mediated initiation of blood coagulation and related phenomena," in Ogston and Bennett, *Haemostasis,* London, New York, Sydney, and Toronto, John Wiley & Sons, 1977, 25-55] and, according to C. J. Paton et al. ["Prekallikrein activator in human albumin," *The Lancet* 3, 747 (1981)] one of the prekallikrein activators (PKA, Hageman-factor fragments) probably responsible for the incidents of decreased blood pressure sometimes observed during rapid infusion of plasma products in blood-product therapy.

In one preferred embodiment of the invention the plasma-protein solution in accordance with the invention is also irradiated with ultraviolet light in an inert-gas atmosphere before or after adsorption onto colloidal silicic acid. The radiation dose is generally 0.5-4 mW/cm$^2$/min. The inert gas may be nitrogen or a noble gas like argon or krypton. Nitrogen is preferred.

One of the most significant problems in the transfusion of fresh plasma is that the solutions can transmit hepatitis [Barker, L. F., "Post-transfusion hepatitis: epidemiology, experimental studies, and US perspective," *Bibliotheca Haem.* 46, 3-14 (1980) and Frösner, G. G., "Nicht-A-nicht-B-Hepatitis," *Munch. med. W.* 122, 7, 229-30 (1980)]. It is known that the risk of transmitting hepatitis through solutions of human plasma-protein solutions can be avoided with combined β-propiolactone and ultraviolet treatment (German Offenlegungsschrift No. 2 902 158) or by treatment with colloidal silicic acid and ultraviolet radiation (German Pat. Nos. 1 617 319 and 1 617 335). There is, however, a drawback to these treatments in the definite or total loss of plasma clotting-factor activity. The method of manufacturing a "fresh plasma" with an extensively decreased fibrinogen content in accordance with the invention allows plasma clotting-factor activity to be largely retained as a result of the protective gas employed in conjunction with the ultraviolet radiation.

Treating the plasmas with β-propiolactone and ultraviolet radiation to avoid the risk of hepatitis from blood products is likewise described in European Pat. No. 14 333, which also discloses the effects of these treatments on the activity of some of the clotting factors in the plasma. Various effects on the activity of a number of clotting factors as the result of the separate steps of β-propiolactone and ultraviolet treatment have also been described [Kotitschke, R. and Stephan, W., *Struktur und Funktion des Fibrinogens,* Stuttgart and New York, Schattauer-Verlag, 1976, 222-28].

Table III shows the effects of treatment with β-propiolactone and ultraviolet with and without an inert-gas atmosphere on the activity of factors V and VIII and antithrombin III in fresh plasma stabilized with citrate and adsorbed with colloidal silicic acid.

TABLE III

Effects of treatment with β-propiolactone and ultraviolet with and without an inert-gas atmosphere on the plasma stabilized with citrate and adsorbed with (2 × 40 mg per gram of protein of) colloidal silicic acid.

| Activity in % of standard | | | bacteriophages |
|---|---|---|---|
| Factor V | Factor VIII | Ant. III | per ml |
| (a) Starting plasma adsorbed with colloidal silicic acid: | | | |
| 95 | 90 | 100 | 6 × 10$^6$ |
| Subsequent to treatment with (0.25%) β-propiolactone: | | | |
| 60 | 60 | 60 | 4 × 10$^4$ |
| (b) Starting plasma adsorbed with colloidal silicic acid: | | | |
| 95 | 90 | 100 | 6 × 10$^6$ |
| Subsequent to (2 mW/cm$^2$/min of) UV radiation in air: | | | |

TABLE III-continued

Effects of treatment with β-propiolactone and ultraviolet with and without an inert-gas atmosphere on the plasma stabilized with citrate and adsorbed with (2 × 40 mg per gram of protein of) colloidal silicic acid.

| Activity in % of standard | | | bacteriophages |
|---|---|---|---|
| Factor V | Factor VIII | Ant. III | per ml |
| 65 | 60 | 65 | 0 |
| Subsequent to (2 mW/cm$^2$/min of) UV radiation under N$_2$: | | | |
| 80 | 75 | 80 | 0 |

The results of ultraviolet radiation of the activity of the sensitive clotting factors V and VII listed in Table II show that, surprisingly, the decrease in the activity of these factors can be significantly reduced by carrying out the radiation in an inert-gas, especially nitrogen, atmosphere.

The results of the bacteriophage tests also shown in Table III indicate that ultraviolet radiation completely inactivates the bacteriophages.

The sequence in which adsorption onto colloidal silicic acid and ultraviolet radiation is carried out has no essential effect on the results. Thus, the pooled plasma can be subjected first to ultraviolet and then to adsorption onto colloidal silicic acid. Ultraviolet radiation can, however, also be left out completely when the risk of hepatitis transmission has been severely reduced by diagnostic measures.

The advantages of the coagulant plasma-protein solution in accordance with the invention over known solutions can be briefly summarized as follows:
1. Large pools of plasma can be manufactured on an industrial scale.
2. Treatment to inactivate virus is possible.
3. The activity of the sensitive plasma factors V and VIII can be retained.
4. Freeze-drying is possible.

The advantages of using the coagulant plasma-protein solution in accordance with the invention can be ascribed to the following facts:
1. The extensive absence of fibrinogen decreases the risk of blocking the microcirculation as the result of fibrin clots.
2. There is no need to test for ABO compatibility.
3. Intolerance reactions as the result of prekallikrein are avoided.

DETAILED DESCRIPTION OF THE PREFERRED EMBODIMENTS

The invention will now be described in the following examples:

EXAMPLE 1

The manufacture of fibrinogen-free coagulant plasma-protein solution 9 parts of venous donor blood were added to 1 part of a 3% sodium-citrate stabilizer solution. The blood was centrifuged directly after being withdrawn to separate the plasma-protein solution from the erythrocytes, which were suspended in a physiological salt solution and reinfused into the donor (plasmapheresis). The plasma was frozen in a cryostat within 2 hours of withdrawal.

The frozen plasma was thawed at a temperature of +37° C. Several plasmas from separate donors were pooled. The pooled plasma was cooled to +4° C. and mixed with colloidal silicic acid (Aerosil 380, Degussa) at a concentration of 0.25 g of silicic acid per 100 ml of plasma, or 40 mg per g of protein, and stirred for 20 minutes. The silicic acid was separated by centrifugation and a second adsorption onto colloidal silicic acid carried out under the same conditions. The plasma-protein solution was subjected to ultraviolet radiation. In so doing, the pH of the solution was adjusted to 7.2 and the solution, at a temperature of 4° C., was irradiated in a nitrogen atmosphere with an ultraviolet flow device at a dosage of 2 mW/cm$^2$/min.

Empty sterile 500 ml-bottles were filled with 250 ml at a time of the ultraviolet-irradiated, low-fibrinogen, plasma-protein solution through 0.45–0.22 μm-pore membrane filters sterilized with hot air.

The filter-sterilized protein solution was spin-frozen in the cryostat and subsequently freeze-dried.

A coagulant plasma-protein solution appropriate for intravenous application and with the properties listed in Table IV was obtained by dissolving the freeze-dried preparation in distilled water to a protein content of 5 g/100 ml.

TABLE IV

Properties of the coagulant plasma-protein solution (protein content of 5 g/100 ml).

|  | Activity in % of standard |
|---|---|
| Factor II | 95 |
| Factor V | 60* |
| Factor VII | 90 |
| Factor VIII | 70* |
| Factor IX | 95 |
| Factor X | 95 |
| Factor XI | 10 |
| Factor XII | 10 |
| Antithrombin III | 80 |
| Fibrinogen (mg/100 ml) | 30 |

*Differences from the data in Table III can be ascribed to losses from filter sterilization, freeze-drying, etc.

EXAMPLE 2

The method described in Example 1 was employed except that heparin was employed to stabilize the venous donor blood instead of the sodium-citrate solution. The resulting starting plasma was treated as described in Example 1 to obtain a coagulant plasma-protein solution containing heparin and with properties like those listed in Table IV.

EXAMPLE 3

The method described in Example 1 was employed except that an ion exchanger was employed to stabilize the venous donor blood instead of the sodium-citrate solution. The ion-exchanger plasma was prepared as described in German Pat. No. 2 459 291. The ion-exchanger plasma was treated as described in Example 1. A coagulant plasma-protein solution with properties like those listed in Table IV was obtained.

EXAMPLE 4

A plasma pool obtained as described in Example 1 was prepared and irradiated with ultraviolet light with an ultraviolet flow device at 2 mW/cm$^2$/min. The ultraviolet-irradiated plasma was cooled to +4° C. and subjected twice to adsorption with colloidal silicic acid as described in Example 1.

Further processing and freeze-drying was also as described in Example 1. The properties of the solution obtained by dissolving the freeze-dried preparation were similar to those in Table IV.

EXAMPLE 5

Citrated plasma was adjusted to a pH of 7.2, cooled to +4° C., and stirred with colloidal silicic acid (Aerosil 380) as described in Example 1. This mixture was frozen at −80° C. The frozen mixture was thawed at +37° C. and the silicic acid separated by centrifuging. The residue was again treated with colloidal silicic acid (Aerosil 380) subject to the aforesaid conditions, the mixture refrozen at −80° C. and thawed at +37° C., and the the silicic acid separated by centrifuging. The twice-adsorbed, low-fibrinogen plasma was filtered sterile, spin-frozen at −40° C., and freeze-dried.

It is understood that the specification and examples are illustrative but not limitatative of the present invention and that other embodiments within the spirit and scope of the invention will suggest themselves to those skilled in the art.

We claim:

1. A method of producing a coagulant plasma-protein solution comprising contacting stabilized human plasma at least once with 20–40 mg of colloidal silicic acid per gram of plasma protein and separating the silicic acid from the solution.

2. A method according to claim 1, including the additional step of irradiating the solution with ultraviolet light in an inert-gas atmosphere before or after the contact with the colloidal silicic acid.

3. A method according to claim 1, wherein the stabilized human plasma is twice contacted with 20–40 mg of colloidal silicic acid per gram of plasma protein.

4. A method according to claim 1, wherein the stabilized human plasma is obtained by stabilizing human blood by adding a citrate stabilizer or heparin or by extracting the calcium ions with an ion exchanger.

5. A method according to claim 1, wherein the silicic acid is separated from the solution by filter sterilization or ultrafiltration.

6. A coagulant plasma-protein solution produced by the process of claim 1.

7. A coagulant plasma-protein solution produced by the process of claim 2.

8. A coagulant plasma-protein solution produced by the process of claim 3.

9. A coagulant plasma-protein solution produced by the process of claim 4.

10. A coagulant plasma-protein solution produced by the process of claim 5.

11. A product produced by freeze drying the product of claim 6.

* * * * *